(12) United States Patent
Zuo et al.

(10) Patent No.: US 7,822,554 B2
(45) Date of Patent: *Oct. 26, 2010

(54) METHODS AND APPARATUS FOR ANALYSIS OF DOWNHOLE COMPOSITIONAL GRADIENTS AND APPLICATIONS THEREOF

(75) Inventors: Youxiang (Julian) Zuo, Edmonton (CA); Moin Muhammad, Katy, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 207 days.

This patent is subject to a terminal disclaimer.

(21) Appl. No.: 12/210,461

(22) Filed: Sep. 15, 2008

(65) Prior Publication Data

US 2009/0235731 A1 Sep. 24, 2009

Related U.S. Application Data

(60) Provisional application No. 61/023,129, filed on Jan. 24, 2008.

(51) Int. Cl.
*G01V 1/40* (2006.01)
(52) U.S. Cl. ............................. 702/6; 706/14; 706/17; 706/18; 706/21; 702/11; 702/13; 250/254; 250/256; 175/58; 175/40
(58) Field of Classification Search .............. 706/14, 706/17, 18, 21; 702/6, 11, 13; 250/254, 250/256; 175/58, 40
See application file for complete search history.

(56) References Cited

U.S. PATENT DOCUMENTS

| | | | |
|---|---|---|---|
| 3,859,851 A | 1/1975 | Urbanosky | |
| 4,994,671 A | 2/1991 | Safinya et al. | |
| 5,167,149 A | 12/1992 | Mullins et al. | |
| 5,201,220 A | 4/1993 | Mullins et al. | |
| 5,266,800 A | 11/1993 | Mullins | |
| 5,331,156 A | 7/1994 | Hines et al. | |
| 6,467,340 B1 | 10/2002 | Gallagher et al. | |
| 7,081,615 B2 | 7/2006 | Betancourt et al. | |
| 7,249,009 B2 | 7/2007 | Ferworn et al. | |
| 7,277,796 B2 * | 10/2007 | Kuchuk et al. | 702/7 |
| 7,305,306 B2 * | 12/2007 | Venkataramanan et al. | 702/9 |
| 7,644,611 B2 * | 1/2010 | Kamiya et al. | 73/152.28 |
| 2002/0016703 A1 | 2/2002 | Barroux | |

(Continued)

OTHER PUBLICATIONS

Pederson, K.S. et al: "Properties of Oils and Natural Gases", Contributions in Petroleum Geology & Engineering, vol. 5, 1989, Gulf Publishing Company.

(Continued)

*Primary Examiner*—Mohamed Charioui
*Assistant Examiner*—Elias Desta
(74) *Attorney, Agent, or Firm*—Jay P. Sbrollini; Wayne I. Kanak

(57) ABSTRACT

A method and system are provided for characterizing a reservoir of interest by comparing measured downhole fluid analysis measurement data with predicted downhole fluid analysis measurement data for the corresponding depth within the reservoir. The downhole fluid analysis measurement data may comprise the results of compositional analysis, gas-oil ratio measurements, and spectrophotometry measurements. The compositional analyses may be delumped to characterize the compositional components of the downhole fluid and equations of state may be used to predict compositional gradients and fluid properties with depth. The method and system enable the user to characterize a reservoir as to its states of compartmentalization and equilibrium.

20 Claims, 3 Drawing Sheets

U.S. PATENT DOCUMENTS

| | | | |
|---|---|---|---|
| 2004/0104341 | A1 | 6/2004 | Betancourt et al. |
| 2007/0119244 | A1 | 5/2007 | Goodwin et al. |
| 2007/0143023 | A1 | 6/2007 | Betancourt et al. |
| 2009/0248310 | A1* | 10/2009 | Zuo et al. .................... 702/11 |

OTHER PUBLICATIONS

Zuo, Julian Youxiang et al: "Hydrate Pahse Equilibrium Calculations for Crude Oils", 5th International Conference on Gas Hydrates Jun. 13-16, 2005, Trondheim, Norway 7.

Zuo, Julian Youxiang et al: "Plus Fraction Characterization and PVT Data Regression for Resevoir Fluids near Critical Conditions", Society of Petroleum Engineers Asia Pacific Oil and Gas Conference and Exhibition, Brisbane, Australia, Oct. 16-18, 2000, SPE 64520.

Zuo, Julian Youxiang et al: "Prediction of Gas Hydrate Formation Conditions in Aqueous Solutions of Single and Mixed Electrolytes", SPE Journal, Dec. 1997, vol. 2, SPE 31048, pp. 406-416.

Zuo, Julian Youxiang et al: "Wax Formation from Synthetic Oil Systems and Reservoir Fluids", Energy & Fuels 2008, vol. 22, pp. 2390-2395.

Aasberg-Petersen, Kim et al: "Prediction of Viscosities of Hydrocarbon Mixtures", Fluid Phase Equilibria, 1991, vol. 70, pp. 293-308.

Alboudwarej, H. et al: "Effective Tuning of Wax Precipitation Models", 7th International Conference on Petroleum Phase Behavior and Fouling, Asheville, North Carolina, Jun. 25-29, 2006.

Almehaideb, Reyadh A. et al: "EOS tuning to model full field crude oil properties using multiple well fluid PVT analysis", Journal of Petroleum Science and Engineering, 2000, vol. 26, pp. 291-300.

Behrens, R.A. et al: "The Use of Semicontinuous Description to Model the C7+ Fraction in Equation of State Calculations", SPE Reservoir Engineering, Aug. 1988, pp. 1041-1047.

Betancourt, S.S. et al: "Exploration Applications of Downhole Measurement of Crude Oil Composition and Fluorescence", Asia Pacific Technical Conference 2003, SPE 87011.

Chorn, Larry G. et al: "C7 Fraction Characterization", Advances in Thermodynamics, vol. 1, 1989 Taylor & Francis New York Inc., pp. 35-56.

Christensen, P.L.: "Regression to Experimental PVT Data", Journal of Canadian Petroleum Technology, Special Edition 1999, vol. 38, No. 13, Paper: 96-10-15, pp. 1-9.

Coats, K.H. et al: "Application of a Regression-Based EOS PVT Program to Laboratory Data", SPE Reservoir Engineering, May 1986, pp. 277-299.

Cotterman, Ronald L. et al: "Flash Calculations for Continuous or Semicontinuous Mixtures Using an Equation of State", Ind. Eng. Chem. Process Des. Dev., 1985, vol. 24, pp. 434-443.

Cotterman, Ronald L. et al: "Phase Equilibria for Mixtures Containing Very Many Components. Development and Application of Continuous Thermodynamics for Chemical Process Design", Ind. Eng. Chem. Process Des. Dev., 1985, vol. 24, pp. 194-203.

Du, James L. et al: "A Thermodynamic Model for the Prediction of Asphaltene Precipitation", Petroleum Science and Technology, 2004, vol. 22, Nos. 7 & 8, pp. 1023-1033.

Dubost, F. et al: "Integration of In-Situ Fluid Measurements for Pressure Gradients Calculations", Society of Petroleum Engineers, 2007, SPE 108494.

Firoozabadi, A.: "Thermodynamics of Hydrocarbon Reservoirs", McGraw Hill, 1999.

Fujisawa, G. et al: "Large Hydrocarbon Compositional Gradient Revealed by In-Situ Optical Spectroscopy", Society of Petroleum Engineers ATCE Houston, Sep. 2004, SPE 89704.

Ghorayeb, Kassem et al: "Interpretation of the Unusual Fluid Distribution in the Yufutsu Gas-Condensate Field", SPE Journal, Jun. 2003, pp. 114-123.

Ghorayeb, K. et al: "Modeling Multicomponent Diffusion and Convection in Porous Media", SPE Journal, 2000, 5(2), pp. 158-171.

Ghorayeb, Kassem et al: "Molecular, Pressure, and Thermal Diffusion in Nonideal Multicomponent Mixtures", AIChE Journal, May 2000, vol. 46, No. 5, pp. 883-891.

Ghorayeb, K. et al: "Numerical Study of Natural Convection and Diffusion in Fractured Porous Media", SPE Journal, 2000, 5(1), pp. 12-20.

Gonzalez, D.L. et al: "Prediction of Asphaltene Instability under Gas Injection with the PC-SAFT Equation of State", Energy * Fuels, 2005, vol. 19, pp. 1230-1234.

Guo, X.-Q. et al: "Viscosity model based on equations of state for hydrocarbon liquids and gases", Fluid Phase Equilibria 139, 1997, pp. 405-421.

Hirschberg, Avraham: "Role of Asphaltenes in Compositional Grading of a Reservoir's Fluid Column", Journal of Petroleum Technology, Jan. 1988, pp. 89-94.

Hoffmann, A.E. et al: "Equilibrium Constants for a Gas-Condensate System", Society of Petroleum Engineers, 1953, vol. 198, SPE 219-G, pp. 1-10.

Hoier, Lars et al: "Compositional Grading—Theory and Practice", Society of Petroleum Engineers, Oct. 2000, pp. 1-16, SPE 63085.

Jhaveri, Bharat S. et al: "Three-Parameter Modification of the Peng-Robinson Equation of State to Improve Volumetric Predictions", Society of Petroleum Engineers, Aug. 1988, SPE 13118, pp. 1033-1040.

Kabir, C.S. et al: "How Reliable is Fluid Gradient in Gas/Condensate Reservoirs", Society of Petroleum Engineers, 2006, SPE 99386.

Katz, D.L. et al: "Predicting Phase Behavoir of Condensate/Crude-Oil Systems Using Methane Interaction Coefficients", Society of Petroleum Engineers, Nov. 1978, SPE 6721, pp. 1649-1655.

Kesler, Michael G. et al: "Improve prediction of enthalpy of fractions", Hydrocarbon Processing, Mar. 1976, pp. 153-158.

Lohrenz, John et al: "Calculating Viscosities of Reservoir Fluids From Their Compositions", Society of Petroleum Engineers, Oct. 1964, SPE 915, pp. 1171-1176.

Manafi, Hussain et al: "Phase behavior prediction of petroleum fluids with minimum characterization data", Journal of Petroleum Science & Engineering, 1999, vol. 22, pp. 67-93.

Montel, Francois et al: "Initial state of petroleum reservoirs: A comprehensive approach", Journal of Petroleum Science & Engineering, Mar. 12, 2006, pp. 391-402.

Montel, Francois et al: "Modeling the Effect of External Gas Flux on Reservoir Fluid Distribution", Society of Petroleum Engineers, Sep.-Oct. 2002, pp. 1-6, SPE 77383.

Montel, Francois et al: "Prediction of Compositional Grading in a Reservoir Fluid Column", Society of Petroleum Engineers, Sep. 1985, pp. 1-12, SPE 14410.

Montel, Francois et al: "Pressure and Compositional Gradients in Reservoirs", Society of Petroleum Engineers, Aug. 2003, pp. 1-8, SPE 85668.

Mullins, O. et al: "Asphaltene Gravitational Gradient in a Deepwater Reservoir as Determined by Downhole Fluid Analysis", Society of Petroleum Engineers, Houston 2007, SPE 106375.

Nasrabadi, H. et al: "Reservoir Initialization in Two-Phase Hydrocarbon Reservoirs from Well PVT Data", Society of Petroleum Engineers, 2005, SPE 95804.

Pedersen, K.S. et al: "Characterization of Gas Condensate Mixtures", C7 Fraction Characterization, Advances in Thermodynamics, vol. 1, 1989 Taylor & Francis New York Inc. pp. 137-151.

Pedersen, K.S. et al: "Modeling of Large Hydrocarbon Compositional Gradient", Society of Petroleum Engineers, Nov. 2006, pp. 1-7, SPE 101275.

Pedersen, K.S. et al: "Simulations of Compositional Gradients in Hydrocarbon Reservoirs Under the Influence of a Temperature Gradient", Society of Petroleum Engineers, Oct. 2003, pp. 1-10, SPE 84364.

Peneloux et al: "A Consistent Correction for Redlich-Kwong-Soave Volumes", Fluid Phase Equilibria, 1982, vol. 8, pp. 7-23.

Peng, D.-Y et al: "A New Two-Constant Equation of State", Ind. End. Chem. Fundam., 1976, vol. 15, pp. 59-64.

Ratulowski, J. et al: "Theoretical and Experimental Investigation of Isothermal Compositional Grading", SPE Reservoir Evaluation & Engineering, Jun. 2003, pp. 168-175.

Riazi, Mohammad R. et al: "Prediction of the Composition of Petroleum Fractions", Ind. Eng. Chem. Process Des. Dev. 1980, vol. 19, pp. 289-294.

Schulte, A.M.: "Compositional Variations Within a Hydrocarbon Column due to Gravity", Society of Petroleum Engineers of AIME, Sep. 1980, pp. 1-10, 9235.

Shorter Communications: "An improved corresponding states model for the prediction of oil and gas viscosities and thermal conductivities", Chemical Engineering Science, 1987, vol. 42, No. 1, pp. 182-186.

Soave, G.: "Equilibrium Constants from a Modified Redlich-Kwong Equation of State", Chemical Engineering Science, 1972, vol. 27, pp. 1197-1203.

Twu, Chorng H.: "An Internally Consistent Correlation for Predicting the Critical Properties and Molecular Weights of Petroleum and Coal-Tar Liquids", Fluid Phase Equilibria, 1984, vol. 16, pp. 137-150.

Whitson, Curtis H. et al: "Application of the Gamma Distribution Model to Molecular Weight and Boiling Point Data for Petroleum Fractions", Chem. Eng. Comm. 1990, vol. 96, pp. 259-278.

Whitson, Curtis H.: "Characterizing Hydrocarbon Plus Fractions", Society of Petroleum Engineers, Aug. 1983, SPE 12233, pp. 683-694.

Whitson, Curtis H.: "Effect of C7 Properties on Equation-of-State Predictions", Society of Petroleum Engineers Journal, Dec. 1984, pp. 685-696.

Zuo, Julian Youxiang et al: "An improved thermodynamic model for wax precipitation from petroleum fluids", Chemical Engineering Science 56 (2001) pp. 6941-6947.

Yinghui, Li and Johns, Russell T.: "Rapid Flash Calculations for Compositional Simulation", Society of Petroleum Engineers, Oct. 2006, SPE 95732.

Smith, Richard W. et al: "Equation of State of a Complex Fluid Column and Prediction of Contacts in Orocual Field, Venezuela", Society of Petroleum Engineers, Oct. 2000, SPE 63088.

Wang, P. et al: "A New Generation EOS Compositional Reservoir Simulator: Part I—Formulation and Discretization", Society of Petroleum Engineers, 1997, SPE 37979.

* cited by examiner

METHODS AND APPARATUS FOR ANALYSIS OF DOWNHOLE COMPOSITIONAL GRADIENTS AND APPLICATIONS THEREOF

CROSS-REFERENCE TO RELATED APPLICATION

This application claims priority from U.S. Provisional Application 61/023,129, filed Jan. 24, 2008, which is incorporated herein by reference.

BACKGROUND OF THE INVENTION

1. Field of the Invention

The present invention relates to methods and apparatus for characterizing petroleum fluid extracted from a hydrocarbon bearing geological formation. The invention has application to reservoir simulation applications, although it is not limited thereto.

2. Description of Related Art

Petroleum consists of a complex mixture of hydrocarbons of various molecular weights, plus other organic compounds. The exact molecular composition of petroleum varies widely from formation to formation. The proportion of hydrocarbons in the mixture is highly variable and ranges from as much as 97% by weight in the lighter oils to as little as 50% in the heavier oils and bitumens. The hydrocarbons in petroleum are mostly alkanes (linear or branched), cycloalkanes, aromatic hydrocarbons, or more complicated chemicals like asphaltenes. The other organic compounds in petroleum typically contain carbon dioxide ($CO_2$), nitrogen, oxygen, and sulfur, and trace amounts of metals such as iron, nickel, copper, and vanadium.

The alkanes, also known as paraffins, are saturated hydrocarbons with straight or branched chains which contain only carbon and hydrogen and have the general formula $C_nH_{2n+2}$. They generally have from 5 to 40 carbon atoms per molecule, although trace amounts of shorter or longer molecules may be present in the mixture. The alkanes include methane ($CH_4$), ethane ($C_2H_6$), propane ($C_3H_8$), i-butane ($iC_4H_{10}$), n-butane ($nC_4H_{10}$), i-pentane ($iC_5H_{12}$), n-pentane ($nC_5H_{12}$), hexane ($C_6H_{14}$), heptane ($C_7H_{16}$), octane ($C_8H_{18}$), nonane ($C_9H_{20}$), decane ($C_{10}H_{22}$), hendecane ($C_{11}H_{24}$)—also referred to as endecane or undecane, dodecane ($C_{12}H_{26}$), tridecane ($C_{13}H_{28}$), tetradecane ($C_{14}H_{30}$), pentadecane ($C_{15}H_{32}$) and hexadecane ($C_{16}H_{34}$).

The cycloalkanes, also known as napthenes, are saturated hydrocarbons which have one or more carbon rings to which hydrogen atoms are attached according to the formula $C_nH_{2n}$. Cycloalkanes have similar properties to alkanes but have higher boiling points. The cycloalkanes include cyclopropane ($C_3H_6$), cyclobutane ($C_4H_8$), cyclopentane ($C_5H_{10}$), cyclohexane ($C_6H_{12}$), and cycloheptane ($C_7H_{14}$).

The aromatic hydrocarbons are unsaturated hydrocarbons which have one or more planar six-carbon rings called benzene rings, to which hydrogen atoms are attached with the formula $C_nH_n$. They lend to burn with a sooty flame, and many have a sweet aroma. Some are carcinogenic. The aromatic hydrocarbons include benzene ($C_6H_6$) and derivatives of benzene, as well as polyaromatic hydrocarbons.

Asphaltenes consist primarily of carbon, hydrogen, nitrogen, oxygen, and sulfur, as well as trace amounts of vanadium and nickel. The C:H ratio is approximately 1:1.2, depending on the asphaltene source. Asphaltenes have been shown to have a distribution of molecular masses in the range of 400 grams/mole to 1500 grams/mole with a maximum around 750 grams/mole. The chemical structure of asphaltene is difficult to ascertain due to its complex nature, but has been studied by existing techniques. It is undisputed that asphaltene is composed mainly of polyaromatic carbon, i.e. polycondensed aromatic benzene units with oxygen, nitrogen, and sulfur, combined with minor amounts of a series of heavy metals, particularly vanadium and nickel which occur in porphyrin structures. Asphaltenes are today widely recognized as soluble, chemically altered fragments of kerogen which migrated out of the source rock during oil catagenesis. Asphaltenes are dispersed in reservoir petroleum fluid as nanoaggregates. Heavy oils and tar sands contain much higher proportions of asphaltenes than do medium-API oils or light oils. Condensates are virtually devoid of asphaltenes.

Computer-based modeling and simulation techniques have been developed for estimating the properties and/or behavior of petroleum fluid in a reservoir of interest. Typically, such techniques employ an equation of state (EOS) model that represents the phase behavior of the petroleum fluid in the reservoir. Once the EOS model is defined, it can be used to compute a wide array of properties of the petroleum fluid of the reservoir, such as: gas-oil ratio (GOR) or condensate-gas ratio (CGR), density of each phase, volumetric factors and compressibility, heat capacity and saturation pressure (bubble or dew point). Thus, the EOS model can be solved to obtain saturation pressure at a given temperature. Moreover, GOR, CGR, phase densities, and volumetric factors are byproducts of the EOS model. Transport properties, such as heat capacity or viscosity, can be derived from properties obtained from the EOS model, such as fluid composition. Furthermore, the EOS model can be extended with other reservoir evaluation techniques for compositional simulation of flow and production behavior of the petroleum fluid of the reservoir, as is well know in the art. For example, compositional simulations can be helpful in studying (1) depletion of a volatile oil or gas condensate reservoir where phase compositions and properties vary significantly with pressure below bubble or dew point pressures, (2) injection of non-equilibrium gas (dry or enriched) into a black oil reservoir to mobilize oil by vaporization into a more mobile gas phase or by condensation through an outright (single-contact) or dynamic (multiple-contact) miscibility, and (3) injection of $CO_2$ into an oil reservoir to mobilize oil by miscible displacement and by oil viscosity reduction and oil swelling.

In the past few decades, fluid homogeneity in a hydrocarbon reservoir has been assumed. However, there is now a growing awareness that fluids are often heterogeneous or compartmentalized in the reservoir. A compartmentalized reservoir consists of two or more compartments that may be in hydraulic communication. Two types of reservoir compartmentalization have been identified, namely vertical and lateral compartmentalization. Vertical compartmentalization usually occurs as a result of faulting or stratigraphic changes in the reservoir, while lateral compartmentalization results from horizontal barriers. Gravity, chemical forces, molecular and thermal diffusion, natural convection, biodegradation, adsorption, and external fluxes can also lead to non-equilibrium hydrocarbon distribution in a reservoir.

Reservoir compartmentalization, as well as non-equilibrium hydrocarbon distribution, can significantly hinder production and can make the difference between an economically-viable field and an economically-nonviable field. Techniques to aid an operator to accurately describe reservoir compartments and their distribution, as well as non-equilibrium hydrocarbon distribution, can increase understanding of such reservoirs and ultimately raise production.

Although the importance of reservoir compartmentalization, as well as non-equilibrium hydrocarbon distribution, on production has been recognized, conventional pressure-depth plots and pressure gradient analysis are still performed with traditional straight-line regression schemes. This process may, however, be misleading as fluid compositional changes and compartmentalization give distortions in the pressure gradients, which result in erroneous interpretations of fluid contacts or pressure seals.

Downhole fluid analysis (DFA) measurements provide a useful tool to determine the compositional gradients at downhole conditions in real time. An example of a well logging tool suitable for capturing fluid samples for compositional data analysis is the Modular Dynamic Formation Tester (MDT) available from Schlumberger Technology Corporation of Sugar Land. Tex., USA. The MDT tool provides a controlled channel of hydraulic communication between the reservoir fluid and the wellbore and allows withdrawal of small amounts of formation fluid through a probe that contacts the reservoir rock (formation). Such downhole fluid sampling is advantageous because the sampling is more accurate downhole. More specifically, in the event that the sampling pressure is above the saturation pressure, the fluid will be in a single phase, ensuring that the original composition is being analyzed. For pressures below the saturation pressure, a measurement of the properties of the liquid phase in the oil zone and the associated gas above it will yield a more accurate sampling than a sample recombined at the surface. Indeed, it may be difficult to retain the sample in the state in which it existed downhole when it is retrieved to surface. Historically, fluid samples collected by well logging tools were brought to the surface for analysis in the laboratory. However, recent developments in the MDT tool have made possible the direct measurement of fluid properties downhole during the pump-out or sampling sequence, which, is referred to herein as "downhole fluid analysis." Details of the MDT tool and its capabilities for downhole fluid analysis may be obtained with reference to commonly owned U.S. Pat. Nos. 3,859,851; 4,994,671; 5,167,149; 5,201,220; 5,266,800; 5,331,156; and 7,081,615, all of which are incorporated herein by reference.

Downhole fluid analysis is advantageous because information is provided in real time, in contrast to a laboratory analysis that may take several days, or surface wellsite analysis that may result in undesirable phase transitions as well as the loss of key constituents. However, the compositional and property gradients (e.g., the compositions of $CO_2$, C1, C2, C3-C5, and C6+, and GOR) measured by DFA tools may not provide information that can be used to accurately detect compartmentalization and/or non-equilibrium hydrocarbon distribution in the reservoir of interest.

BRIEF SUMMARY OF THE INVENTION

It is therefore an object of the invention to provide methods and apparatus for downhole fluid analysis that are able to accurately detect compartmentalization and/or non-equilibrium hydrocarbon distribution in the reservoir of interest.

It is yet another object of the invention to provide methods and apparatus for downhole fluid analysis that predict compositional content with depth and use such predictions to compare against downhole measurements associated therewith in order to accurately detect compartmentalization and/or non-equilibrium hydrocarbon distribution in the reservoir of interest.

It is still another object of the present invention to provide methods and apparatus for interpreting downhole fluid analysis to estimate downhole compositional components over depth using an equation-of-state (EOS) approach, and for determining compartmentalization or non-equilibrium of the reservoir based on such estimates.

In accord with the objects of the invention, a downhole fluid analysis tool is employed to perform compositional measurements at one measurement station (reference point) and possibly other measurement stations within a wellbore traversing a reservoir of interest. Compositional gradients with depth can be predicted with equations of state (EOS) that take into account the impacts of gravitational forces, chemical forces, thermal diffusion, etc. The predicted compositional data and compositional data measured by the DFA tool at the corresponding depth can then be compared to one another to determine reservoir properties (such as compartmentalization or non-equilibrium, and layer connectivity or equilibrium).

Additional objects and advantages of the invention will become apparent to those skilled in the art upon reference to the detailed description taken in conjunction with the provided figures.

DETAILED DESCRIPTION OF THE INVENTION

Figure 1:
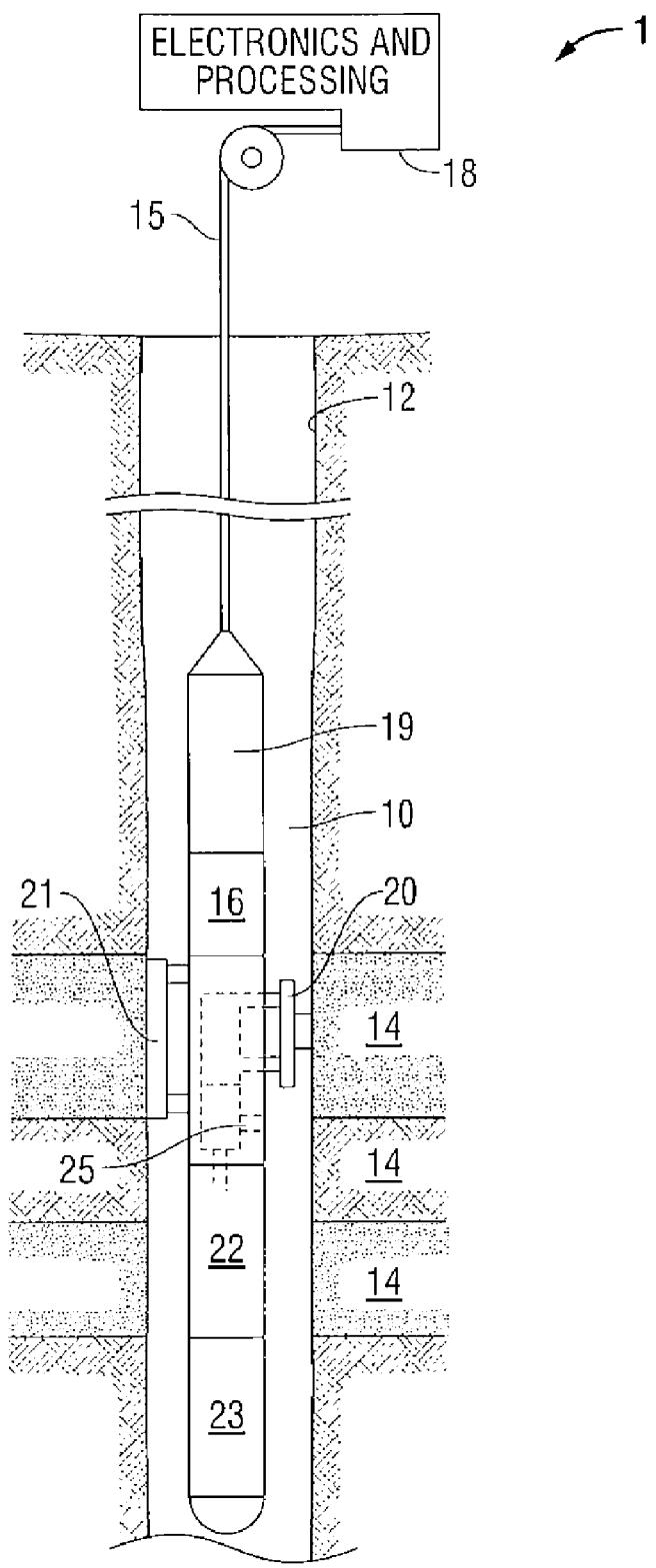
FIG. 1 is a schematic diagram of an exemplary petroleum reservoir analysis system in which the present invention is embodied.

FIG. 1 illustrates an exemplary petroleum reservoir analysis system 1 in which the present invention is embodied. The system 1 includes a borehole tool 10 suspended in the borehole 12 from the lower end of a typical multiconductor cable 15 that is spooled on a suitable winch (not shown) on the formation surface. The cable 15 is electrically coupled to an electronics and processing system 18 on the formation surface. The borehole tool 10 includes an elongated body 19 which encloses the downhole portion of the tool control system 16. The elongated body 19 also carries a selectively extendable fluid admitting assembly 20 and a selectively extendable tool anchoring member 21 which are respectively arranged on opposite sides of the tool body. The fluid admitting assembly 20 is equipped for selectively sealing off or isolating selected portions of the wall of the borehole 12 such that pressure or fluid communication with the adjacent earth formation 14 is established. Also included with tool 10 are means for determining the downhole pressure and temperature (not shown) and a fluid analysis module 25 through which the obtained fluid flows. The fluid may thereafter be expelled through a port (not shown) or it may be sent to one or more fluid collecting chambers 22 and 23 which may receive and retain the fluids obtained from the formation. Control of the fluid admitting assembly 20, the fluid analysis module 25, and the flow path to the collecting chambers is maintained by the tool control system 16 and the electronics and processing system 18. As will be appreciated by those skilled in the art, the surface-located electronics and processing system 18 includes data processing functionality (e.g., one or more microprocessors, associated memory, and other hardware and/or software) to implement the invention as described herein. The electronics and processing system 18 can also be realized by a distributed data processing system wherein data measured by the tool 10 is communicated (preferably in real-time) over a communication link (typically a satellite link) to a remote location for data analysis as described herein. The data analysis can be carried out on a workstation or other suitable data processing system (such as a computer cluster or computing grid).

The DFA tool of FIG. 1 measures concentrations of hydrocarbon components (e.g., methane ($CH_4$), and ethane ($C_2H_6$)) as well as the C3-C5 alkane group, and the lump of hexane and heavier alkane components (C6+). Such measurements are based on spectrophotometry measurements (i.e., the absorption spectra of the downhole fluid sample). In accordance with the present invention, the apparatus of FIG. 1 is employed to perform compositional measurements at one measurement station (reference point) and possibly other measurement stations within a wellbore traversing a reservoir of interest. Compositional gradients with depth can be predicted with equations of state (EOS) that take into account the impacts of gravitational forces, chemical forces, thermal diffusion, etc. The predicted compositional data and compositional data measured by the DFA tool at the corresponding depth can then be compared to one another to determine reservoir compartmentalization or non-equilibrium.

Figure 2A:
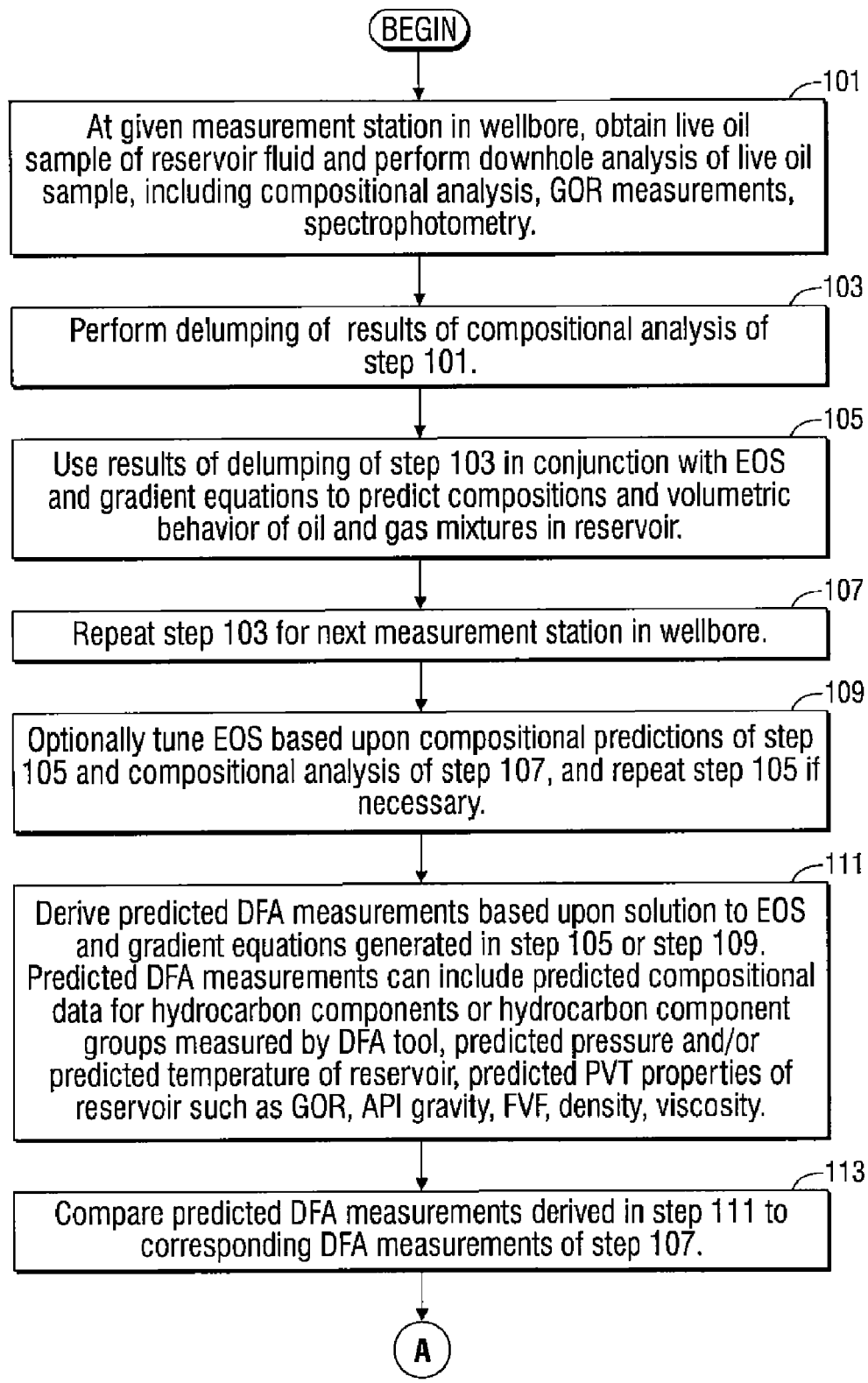
FIGS. 2A and 2B, collectively, are a flow chart of data analysis operations that includes downhole fluid analysis that measures compositional components of acquired reservoir fluid samples. Compositional gradients and fluid properties with depth are predicted from the output of such analysis and a comparison of predicted compositional data and compositional data measured by downhole fluid analysis at the corresponding depth is used to accurately detect compartmentalization and/or non-equilibrium hydrocarbon distribution in the reservoir of interest.
Figure 2B:
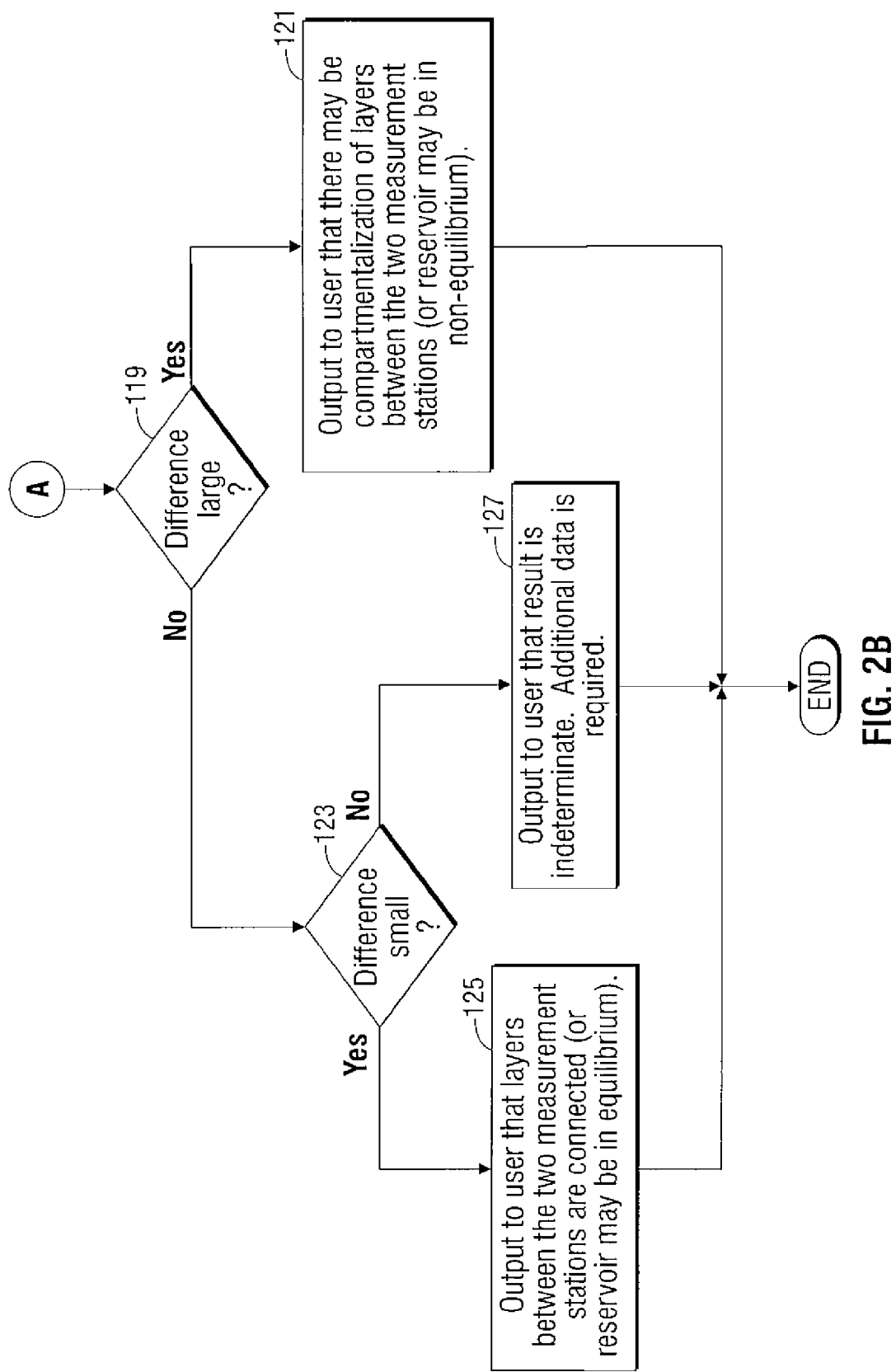

Turning now to FIGS. 2A and 2B, an exemplary methodology for determining reservoir compartmentalization or non-equilibrium in accordance with the present invention is shown. The operations begin in step 101 by employing the DFA tool of FIG. 1 to obtain a sample of the formation fluid at the reservoir pressure and temperature at a measurement station in the wellbore (for example, a reference station). The sample is processed by the fluid analysis module 25. In the preferred embodiment, the fluid analysis module 25 performs spectrophotometry measurements that measure absorption spectra of the sample and translates such spectrophotometry measurements into concentrations of several alkane components and groups in the fluids of interest. In an illustrative embodiment, the fluid analysis module 25 provides measurements of the concentrations (e.g., weight percentages) of carbon dioxide ($CO_2$), methane ($CH_4$), ethane ($C_2H_6$), the C3-C5 alkane group including propane, butane, pentane, and the lump of hexane and heavier alkane components (C6+). The tool 10 also preferably provides a means to measure the temperature of the fluid sample (and thus reservoir temperature at the station), pressure of the fluid sample (and thus reservoir pressure at the station), live fluid density of the fluid sample, gas-oil ratio (GOR) of the fluid sample, API gravity of the fluid sample, formation volume factor (FVF) of the fluid sample, and viscosity of the fluid sample.

In step 103, a delumping process is carried out to characterize the compositional components of the sample analyzed in step 101. Details of the exemplary delumping operations carried out as part of step 103 are described in U.S. patent application Ser. No. 12/209,050, filed on Sep. 11, 2008, herein incorporated by reference in its entirety.

In step 105, the results of the delumping process of step 103 are used in conjunction with equations of state (EOS) to predict compositional gradients with depth that take into account the impacts of gravitational forces, chemical forces, thermal diffusion, etc.

The EOS of step 105 includes a set of equations that, represent, the phase behavior of the compositional, components of the reservoir fluid. Such equations can take many forms. For example, they can be any one of many cubic EOS, as is well known. Such cubic EOS include van der Waals EOS (1873), Redlich-Kwong EOS (1949). Soave-Redlich-Kwong EOS (1972), Peng-Robinson EOS (1976). Stryjek-Vera-Peng-Robinson EOS (1986) and Patel-Teja. EOS (1982). Volume shift parameters can be employed as part of the cubic EOS in order to improve liquid density predictions, as is well known. Mixing rules (such as van der Waals mixing rule) can also be employed as part of the cubic EOS. A statistical associating fluid theory, SAFT-type, EOS can also be used, as is well known in the art.

The EOS of step 105 are extended to predict compositional gradients with depth that take into account the impacts of gravitational forces, chemical forces, thermal diffusion, etc. To calculate compositional, gradients with depth in a hydrocarbon reservoir, it is usually assumed that there are no adsorption phenomena or any kind of chemical reactions in the reservoir. The mass flux (J) of component i that crosses the boundary of an elementary volume of the porous media is expressed as:

$$J_i = \rho_i \left( \sum_{j=1}^{n} (L_{ij} \nabla_T g_j^t) + L_{ip}(\rho g - \nabla P) + L_{iq} \nabla T \right) \quad (1)$$

where $L_{ij}$, $L_{ip}$, and $L_{iq}$ are the phenomenological coefficients, $\rho_i$ denotes the partial density of component i, $\rho$, g, P, T are the density, the gravitational acceleration, pressure, and temperature, respectively, and $g_j^t$ is the contribution of component j to mass free energy of the fluid in a porous media, which can be divided into a chemical potential part $\mu_i$ and a gravitational part gz (where z is the vertical depth).

The average fluid velocity (u) is estimated by:

$$u = \frac{\sum_{j=1}^{n} J_j}{\rho} \quad (2)$$

According to Darcy's law, the phenomenological baro-diffusion coefficients must meet the following constraint:

$$\frac{k}{\eta} = \frac{\sum_{j=1}^{n} \rho_j L_{jp}}{\rho} \quad (3)$$

where k and $\eta$ are the permeability and the viscosity, respectively.

If the pore size is far above the mean free path of molecules, the mobility of the components, due to an external pressure field, is very close to the overall mobility. The mass chemical potential is a function of mole fraction (x), pressure, and temperature. At constant temperature, the derivative of the mass chemical potential ($\mu_j$) has two contributions:

$$\nabla_T \mu_j = \sum_{k=1}^{n} \left(\frac{\partial \mu_j}{\partial x_k}\right)_{T,P,x_{j=1}} \nabla x_k + \left(\frac{\partial \mu_j}{\partial P}\right)_{T,x} \nabla P \quad (4)$$

where the partial derivatives can be expressed in terms of EOS (fugacity coefficients):

$$\left(\frac{\partial \mu_j}{\partial x_k}\right)_{T,P,x_{j=1}} = \frac{RT}{M_j}\left(\frac{\partial \ln f_j}{\partial x_k}\right)_{T,P,x_{j=1}} \quad (5)$$

$$= \frac{RT}{M_j}\left(\frac{\delta_{jk}}{x_k} + \frac{1}{\varphi_j}\left(\frac{\partial \varphi_j}{\partial x_k}\right)_{T,P,x_{j=1}}\right)$$

$$\left(\frac{\partial \mu_j}{\partial P}\right)_{T,x} = \frac{\bar{v}_j}{M_j} \quad (6)$$

$$= \frac{RT}{M_j}\left(\frac{1}{P} + \left(\frac{\partial \varphi_j}{\partial P}\right)_{T,x}\right)$$

where $M_j$, $f_j$, $\varphi_j$, and $v_j$ are the molecular weight, fugacity, fugacity coefficient, and partial molar volume of component j, respectively;

$x_k$ is the mole fraction of component k;

R denotes the universal gas constant; and $\delta$ is the Kronecker delta function.

In the ideal case, the phenomenological coefficients (L) can be related to effective practical diffusion coefficients ($D_i^{eff}$):

$$L_{ii} = -\frac{M_i}{RT} D_i^{eff}. \quad (7)$$

The mass conservation for component i in an n-component reservoir fluid, which governs the distribution of the components in the porous media, is expressed as:

$$\frac{\partial \rho_i}{\partial t} + \nabla J_i = 0, \quad i = 1, 2, \ldots, n. \quad (8)$$

The equation can be used to solve a wide range of problems. This is a dynamic model which is changing with time t.

Consider that the mechanical equilibrium of the fluid column has been achieved:

$$\nabla_z P = \rho g. \quad (9)$$

The vertical distribution of the components can be calculated by solving the following set of equations:

$$\frac{\partial \ln f_i}{\partial z} - \frac{M_i g}{RT} + \frac{J_{i,z}}{x_i D_i^{eff}} \frac{M}{\rho M_i} - \frac{L_{iq}}{D_i^{eff}} \frac{\partial T}{\partial z} = 0, \quad (10)$$

$i = 1, 2, \ldots, n$ and $$\sum_{k=1}^{n} \left(\frac{\delta_{ik}}{x_k} + \frac{1}{\varphi_i}\frac{\partial \varphi_i}{\partial x_k}\right) \nabla_z x_k + \frac{(v_i \rho - M_i)g}{RT} + \frac{J_{i,z}}{x_i D_i^{eff}} \frac{M}{\rho M_i} - \frac{L_{iq}}{D_i^{eff}} \frac{\partial T}{\partial z} = 0 \quad (11)$$

where $J_{i,z}$ is the vertical component of the external mass flux.

This formulation allows computation of the stationary state of the fluid column and it does not require modeling of the dynamic process leading to the observed compositional distribution.

If the horizontal components of external fluxes are significant, the equations along the other axis have to be solved as well. Along a horizontal "x" axis the equations become:

$$\frac{\partial \ln f_i}{\partial x} + \frac{J_{i,x}}{x_i D_i^{eff}} \frac{M}{\rho M_i} - \frac{L_{iq}}{D_i^{eff}} \frac{\partial T}{\partial x} = 0 \quad (12)$$

The mechanical equilibrium of the fluid column $\nabla_z P = \rho g$, is a particular situation which will occur only in highly permeable reservoirs. In the general case, the vertical pressure gradient is calculated by:

$$\nabla_z P = \rho g - \frac{\nabla_z P_{Fluxes} + \nabla_z P_{Soret}}{1 + R_p} \quad (13)$$

where $R_p$ is calculated by $$R_p = RT \frac{k}{\eta} \frac{\rho}{M} \sum_{i=1}^{n} \frac{x_i}{D_i^{eff}}. \quad (14)$$

The pressure gradient contribution from thermal diffusion (so-called Soret contribution) is given by:

$$\nabla_z P_{Soret} = RT \frac{\rho}{M} \sum_{i=1}^{n} x_i \frac{L_{iq}}{D_i^{eff}} \nabla_z T. \quad (15)$$

And the pressure gradient contribution from external fluxes is expressed as $$\nabla_z P_{Fluxes} = RT \sum_{i=1}^{n} \frac{J_{i,z}}{M_i D_i^{eff}}. \quad (16)$$

Assuming an isothermal reservoir and ignoring the external flux, results in the following equation:

$$\frac{\partial \ln f_i}{\partial z} - \frac{M_i g}{RT} = 0, \quad i = 1, 2, \ldots, n \quad (17)$$

Equation (17) can be rewritten, for the non-isothermal case, as $$\frac{\partial \ln f_i}{\partial z} - \frac{M_i g}{RT} + a_i = 0, \quad i = 1, 2, \ldots, n \quad (18)$$

where $a_j$ is computed by:

$$a_i = \frac{J_{i,z}}{x_i D_i^{\text{eff}}} \frac{M}{\rho M_i} - \frac{L_{iq}}{D_i^{\text{eff}}} \frac{\partial T}{\partial z}, \quad i = 1, 2, \ldots, n. \quad (19)$$

In step 107, the DFA tool of FIG. 1 is used to obtain a sample of the formation fluid at the reservoir pressure and temperature at another measurement station in the well bore and the downhole fluid analysis as described above with respect to step 101 is performed on this sample. In die preferred embodiment, the fluid analysis module 25 performs spectrophotometry measurements that measure absorption spectra of the sample and translates such spectrophotometry measurements into concentrations of several alkane components and groups in the fluids of interest. The tool also preferably provides a means to measure temperature of the fluid sample (and thus reservoir temperature at the station), pressure of the fluid sample (and thus reservoir pressure at the station), live fluid density of the fluid sample, gas-oil ratio (GOR) of the fluid sample, API gravity of the fluid sample, formation volume factor (FVF) of the fluid sample, and viscosity of the fluid sample.

Optionally, in step 109 the EOS of step 105 are tuned based on a comparison of the compositional analysis of the DFA tool in step 107 and the predictions of composition gradient with depth derived by the EOS of step 105. In the event, that the EOS is tuned, the compositional gradient and fluid property predictions of step 105 can be recalculated from the tuned EOS, Tuning of the EOS of step 105 typically involves tuning volume translation parameters, binary interaction parameters, and/or critical properties of the components of the EOS. An example of EOS tuning is described in Reyadh A. Almehaideb et al., "EOS timing, to model mil field crude oil properties using multiple well fluid PVT analysis," *Journal of Petroleum Science and Engineering*, Volume 26, Issues 1-4, pages 291-300, 2000, herein incorporated by reference in its entirety.

In step 111, predicted DFA measurements are derived from the EOS and gradient equations generated in step 105 or step 109. The predicted DFA measurements can include predicted compositional data for hydrocarbon components or hydrocarbon component groups measured by the DFA tool, predicted pressure and/or predicted temperature of the reservoir, and predicted PVT properties of the reservoir such as GOR. API gravity, FVF, density, and viscosity. The predicted compositional, pressure, and temperature data at each depth are obtained by solving Equations 18 and 19. The PVT properties are then estimated by the EOS and viscosity models.

In step 113, the predicted DFA measurements derived in 111 are compared to corresponding DFA measurements made by the DFA tool in step 107.

In step 119, the operations check whether the difference result of the comparison of step 113 exceeds predetermined threshold(s) $T_c$. The threshold(s) $T_c$ are selected to identify layer compartmentalization or non-equilibrium of the reservoir from large differences between the predicted DFA measurements and corresponding DFA measurements made by the DFA tool in step 107. If so, the operations continue to step 121 to report to the operator that there may be compartmentalization of the layers between the two measurement stations. It is also possible to report to the user that the reservoir may be in non-equilibrium.

If in step 119 the difference result of the comparison of step 113 does not exceed the predetermined threshold(s) $T_c$, the operations continue to step 123 to check whether the difference result of the comparison of step 113 is less than predetermined threshold(s) $T_c$. The threshold(s) $T_c$ are selected to identify layer connectivity and/or equilibrium of the reservoir from small differences between the predicted DFA measurements and corresponding DFA measurements made by the DFA tool in step 107. If so, the operations continue to step 125 to report to the operator that the layers between the two measurement stations are connected. It is also possible to report to the user that the reservoir may be in equilibrium. If not, the operations continue to step 127 to report to the operator that the result is indeterminate and that additional data is required for clarification.

Note that the operations of steps 101-127 can be repeated as required for multiple station pairs within the borehole to provide for analysis of reservoir compartmentalization for multiple layers of the reservoir.

The process described above is applied to a single well. However, the process can be extended to multiple welts. To accomplish this, the process for a single well is first used to establish the EOS model. The EOS model can then be applied to perform the log predictions for other wells in the same reservoir. The methodologies described above with respect to a single well can be used to compare DFA measurements with the EOS log predictions, and to determine the compartmentalization of the reservoir and/or non-equilibrium distribution of hydrocarbon fluids.

There have been described and illustrated herein preferred embodiments of methods and apparatus for analysis of compositional gradients and applications thereof. While particular embodiments of the invention have been described, it is not intended that the invention be limited thereto, as it is intended that the invention be as broad in scope as the art will allow and that the specification be read likewise. Thus, while particular data processing methodologies and systems have been disclosed, it will be understood that other suitable data processing methodologies and systems can be similarly used. Also, while particular equations of state and applications of such EOS have been disclosed for predicting properties of reservoir fluid, it will be appreciated that other equations of state and applications thereof could be used as well. It will therefore be appreciated by those skilled in the art that yet other modifications could be made to the provided invention without deviating from its scope as claimed.

What is claimed is:

1. A method for characterizing a reservoir of interest comprising:
    (a) obtaining a first reservoir fluid sample at a first downhole measurement station within a borehole that traverses the reservoir of interest;
    (b) performing downhole fluid analysis, DFA, of the first reservoir fluid sample to obtain DFA measurement data characterizing the first reservoir fluid sample;
    (c) predicting compositional components and fluid properties with depth using the results of the downhole fluid analysis of (b);
    (d) obtaining a second reservoir fluid sample at a second downhole measurement station within the borehole;
    (e) performing downhole fluid analysis of the second reservoir fluid sample to obtain DFA measurement data related to the second reservoir fluid sample;

(f) deriving predicted DFA measurement data for reservoir fluid at the second downhole measurement station based upon the compositional components and fluid properties with depth predicted in (c);

(g) comparing the DFA measurement data of (e) and the predicted DFA measurement data of (f); and (h) generating output to the user that characterizes the reservoir of interest based upon the comparing of (g).

2. A method according to claim 1, further comprising repeating steps (a)-(g) over a plurality of downhole measurement station pairs in order to generate output to the user that characterizes the reservoir of interest based upon the comparing of (g) for the plurality of downhole measurement station pairs.

3. A method according to claim 1, wherein the predicting of (c) involves a delumping process that characterizes the compositional components of the respective sample.

4. A method according to claim 1, wherein the predicting of (c) employs equations of state to predict compositional gradients and fluid properties with depth.

5. A method according to claim 1, wherein the downhole fluid analysis of (b) and (e) employs spectrophotometry.

6. A method according to claim 1, wherein the measured and predicted DFA measurement data includes concentrations of carbon dioxide ($CO_2$), methane ($CH_4$), ethane ($C_2H_6$), and the C3-C5 alkane group including propane, butane, and pentane.

7. A method according to claim 6, wherein the measured and predicted DFA measurement data further includes concentrations of the lump of hexane and heavier alkane components (C6+).

8. A method according to claim 1, wherein the measured and predicted DFA measurement data includes temperature, pressure, live fluid density, gas-oil ratio (GOR), API gravity, formation volume factor (FVF), and viscosity.

9. A method according to claim 1, wherein the output relates to at least one of compartmentalization and non-equilibrium of the reservoir.

10. A method according to claim 1, wherein the output relates to at least one of connection of layers and equilibrium of the reservoir.

11. A system for characterizing a reservoir of interest, the system comprising:

(a) downhole tool means for obtaining at least first and second reservoir fluid samples at first and second downhole measurement stations, respectively, within a borehole that traverses the reservoir of interest, the tool comprising means for performing downhole fluid analysis, DFA, of the first and second reservoir fluid samples to obtain DFA measurement data that characterizes compositional components and fluid properties of the first and second reservoir fluid samples;

(b) means for predicting DFA measurement data that characterizes compositional components and fluid properties of the second reservoir fluid sample based upon the DFA measurement data of the downhole fluid analysis related to the first reservoir fluid sample;

(c) means for comparing the DFA measurement data generated by the tool means (a) as part of analysis of the second reservoir fluid sample and the predicted DFA measurement data of means (b); and (d) means for generating output to the user that characterizes the reservoir of interest based upon the comparing of means (c).

12. A system according to claim 11, wherein the means (a)-(c) are operated over a plurality of downhole measurement station pairs in order to generate output to the user that characterizes the reservoir of interest based upon the comparing of means (c) for the plurality of downhole measurement station pairs.

13. A system according to claim 11, wherein the predicting means (b) involves a delumping process that characterizes the compositional components of the respective sample.

14. A system according to claim 11, wherein the predicting means (b) employs equations of state to predict compositional and fluid properties with depth.

15. A system according to claim 11, wherein the downhole fluid analysis of means (a) employs spectrophotometry.

16. A system according to claim 11, wherein the measured and predicted DFA measurement data includes concentrations of carbon dioxide ($CO_2$), methane ($CH_4$), ethane ($C_2H_6$), and the C3-C5 alkane group including propane, butane, pentane.

17. A system according to claim 16, wherein the measured and predicted DFA measurement data includes concentrations of the lump of hexane and heavier alkane components (C6+).

18. A system according to claim 11, wherein the measured and predicted DFA measurement data includes temperature, pressure, live fluid density, gas-oil ratio (GOR), API gravity, formation volume factor (FVF), and viscosity.

19. A system according to claim 11, wherein the output relates to at least one of compartmentalization and non-equilibrium of the reservoir.

20. A system according to claim 11, wherein the output relates to at least one of connection of layers and equilibrium of the reservoir.

* * * * *